United States Patent
McCarthy et al.

(10) Patent No.: US 6,269,679 B1
(45) Date of Patent: Aug. 7, 2001

(54) SYSTEM AND METHOD TO CHARACTERIZE GAS TRANSPORT PROPERTIES

(75) Inventors: Michael R. McCarthy, San Diego; Robert M. Winslow, La Jolla; Kim D. Vandegriff, San Diego, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/509,383

(22) PCT Filed: Oct. 16, 1998

(86) PCT No.: PCT/US98/21813

§ 371 Date: Mar. 24, 2000

§ 102(e) Date: Mar. 24, 2000

(87) PCT Pub. No.: WO99/21002

PCT Pub. Date: Apr. 29, 1999

Related U.S. Application Data

(60) Provisional application No. 60/062,244, filed on Oct. 17, 1997.

(51) Int. Cl.[7] .............. A61B 19/00; G01N 7/00
(52) U.S. Cl. ............ 73/19.1; 73/64.47; 600/323; 600/364
(58) Field of Search ................ 73/19.1, 64.47; 600/364, 323; 422/68.1; 96/202

(56) References Cited

U.S. PATENT DOCUMENTS

| 3,518,982 | * 7/1970 | Timmins et al. ............ 73/19.1 |
| 4,209,300 | 6/1980 | Thibault . |
| 5,058,416 | 10/1991 | Engelhardt et al. . |

FOREIGN PATENT DOCUMENTS

| 2430898 | * 1/1976 | (DE) . |
| 0340908 | * 4/1989 | (EP) .................. 600/364 |
| 0 478 048 | 4/1992 | (EP) . |
| 02124445 | * 5/1990 | (JP) .................. 73/19.1 |

* cited by examiner

*Primary Examiner*—Hezron Williams
*Assistant Examiner*—Michael Cygan
(74) *Attorney, Agent, or Firm*—Brown, Martin, Haller & McClain, LLP

(57) ABSTRACT

An artificial capillary testing apparatus (ACTA) is provided for evaluation of gas transport/exchange properties of a fluid. A sample fluid, having a known of measured partial gas pressure, is introduced from a gas-tight dispenser into an artificial capillary of known diameter located within an exchange chamber containing a flowing exchange gas. The artificial capillary is formed from a permeable material which permits gas exchange between the interior and exterior of the capillary. After exit from the artificial capillary, the effluent fluid is collected in a gas-tight collection cell, then removed from the apparatus to a gas analyzer to measure partial gas pressure, The dispenser, exchange chamber and collection cell are all enclosed within a temperature controlled cabinet, useful in measurement of oxygen transport properties of hemoglobin in blood or blood-substitutes. Flowmeters and other measurement devices can be inserted along the pathway upstream and/or downstream of the artificial capillary to provide additional data. The amount of target gas transferred out of the capillary for a given length is calculated as a function of the gas diffusion constant, the partial gas pressure gradient, the capillary radius and length, the flow rate, and the distribution of gas in its various phases. For evaluation of hemoglobin-based oxygen carriers, an empirical diffusion constant is calculated as a function of the diffusion in $O_2$ partial pressure at the capillary, the Hb concentration, the flow rate, the known oxygen equilibrium curve (OEC) of the sample, and the cross-sectional area and length of the capillary.

33 Claims, 6 Drawing Sheets

SYSTEM AND METHOD TO CHARACTERIZE GAS TRANSPORT PROPERTIES

RELATED APPLICATIONS

This application, in part, claims the benefit of priority under 35 U.S.C.§119(e) to U.S. provisional application Ser. No. 60/062,244, filed Oct. 17, 1997, the subject matter of which is incorporated herein by reference.

FIELD OF INVENTION

The present invention relates to a system and method for the characterization of gas transport properties, and applications therefore.

BACKGROUND

The world-wide need for donated blood is enormous. It was recently estimated that there is a world-wide shortage of donated blood in the area of 200 million units per year. While approximately 11 million units of blood are transfused in the United States each year, the number would be larger were it not for the concern about the transmission of infectious disease. Even with the extensive screening that is now performed on all donated blood, patients and their physicians still fear a repeat of the events of the 1980's, when many people were infected by HIV-contaminated blood. Approximately two-thirds of the donated blood in the U.S. is used during surgery, while the remainder is used in cases of emergency and for people with chronic anemia and other blood related ailments.

While the market remains essentially undeveloped in the U.S., a safe, effective and inexpensive blood substitute product could replace two-thirds of the transfusions, specifically in cases of surgery. Past research has demonstrated that the properties of surface-modified hemoglobin substitutes can be manipulated to provide improved blood flow to organs. See for example, U.S. Pat. No. 5,814,601, of Winslow, et al., which discloses a blood substitute with an oxygen-carrying component, the disclosure of which is incorporated herein by reference. However, in spite of the availability of blood substitutes, as yet, an inexpensive and reliable means for evaluating the properties of such blood substitutes has not been available.

Blood serves a duel function in the process of gas exchange within the body. It is responsible for the transport of oxygen to cells and tissue for aerobic metabolism. Secondly, blood functions to remove carbon dioxide, a by-product of aerobic metabolism, through the lungs. Failure to adequately perform these functions would result in eventual and inevitable cell death. In order for blood to successfully provide much-needed nutrients, as well as remove waste products from within the body, certain hemodynamic properties must be present. Fluid without the proper physicochemical properties will not function in the cardiovascular system.

Hemoglobin is the fundamental molecule for oxygen transport by blood. Hemoglobin is composed of four subunits, each subunit possessing an iron-containing heme group which is responsible for oxygen binding. With these four subunits, one hemoglobin molecule is capable of binding four oxygen molecules. Analysis of the hemoglobin-oxygen interaction is facilitated by plotting numerical blood saturation values against oxygen partial pressure, resulting in an oxygen equilibrium curve (OEC). The shape of the OEC is an important indicator of the ability of a blood sample to transport and deliver oxygen properly. Oxygen delivery needs to be precise. Early release will waste oxygen, and delivery of too much oxygen is believed to have detrimental effects on the vascular system including vasoconstriction and free radical production. In the design and evaluation of blood substitutes, the ability to emulate the precise delivery of oxygen by red blood cells is an important function that must be taken into consideration.

Successful and efficient gas transport is the first design consideration when developing a blood substitute. In natural blood systems, $O_2$ and $CO_2$ are transported by both convection and diffusion processes. Traditionally, analyses of hemoglobin-based oxygen carriers (HBOCs) have been done at equilibrium, thereby relying on the specific OEC. Further, these analyses have shed light on how HBOC effect vasoactivity in arterioles. The transfusion of HBOC into animal models have produced complex results but the dynamic properties of the cardiovascular system has made the analysis of gas transport properties difficult to obtain. Accordingly, a need remains for a method to analyze oxygen delivery by hemoglobin-based blood substitutes which simulates the physiological properties of the cardiovascular system while being completely removed from that system.

SUMMARY OF THE INVENTION

An object of the present invention is to provide a system and method for the characterization of the diffusional gas transport properties of a fluid.

Another object of the present invention is to provide a system and method to characterize the gas transport properties of hemoglobin-based oxygen carriers.

Still another object of the present invention is to provide a method for the evaluation of gas transport properties of cell-free hemoglobins with respect to their ability to augment diffusive oxygen transport.

The artificial capillary testing apparatus (ACTA) of the present invention is designed to evaluate the gas transport/exchange properties of HBOC in isolation from physiological systems, while retaining the dynamics of convection and diffusion inherent in blood-gas transport systems.

Yet another object of the present invention is to provide a method to evaluate the amount of oxygen delivered by any given cell-free hemoglobin as a function of diffusion, hemoglobin concentration, and parameters defining any hemoglobin OEC, i.e., Adair constants.

In an exemplary embodiment, an artificial capillary testing apparatus (ACTA) is provided for evaluation of gas transport/exchange properties of a fluid. A sample fluid, having a known or measured partial gas pressure, is introduced from a gas-tight dispenser into an artificial capillary of known diameter located within an exchange chamber containing a flowing exchange gas. The artificial capillary is formed from a permeable material which permits gas exchange between the interior and exterior of the capillary. After exit from the artificial capillary, the effluent fluid is collected in a gas-tight collection cell, then removed from the apparatus to a gas analyzer to measure partial gas pressure. The dispenser, exchange chamber and collection cell are all enclosed within a temperature controlled cabinet. Monitoring of the environmental conditions within the exchange chamber is performed to confirm purity of the exchange gas. Flowmeters and other measurement devices can be inserted along the pathway upstream and/or downstream of the artificial capillary for monitoring or to provide additional data.

The amount of target gas transferred out of the capillary for a given length is calculated as a function of the gas diffusion constant, the partial gas pressure gradient, the capillary radius, the flow rate, and the distribution of gas in its various phases.

For use in measurement of oxygen transport properties of hemoglobin in blood or blood-substitutes, the apparatus is maintained at body temperature (37° C.) by providing temperature monitoring and controlling apparatus within the cabinet. The fluid is introduced using a gas-tight syringe after equilibrating the solution with humidified air, and calculating the partial oxygen pressure from the barometric pressure minus the water vapor pressure at 37° C. The fluid is pumped into the capillary at a predetermined flow rate to provide a specific residence time, initially with an air-equilibrated environment in the exchange chamber to confirm equal $PO_2$ at the entry and exit points. Humidified nitrogen at 37° C. is then admitted into the exchange chamber until no oxygen is detectable within the exchange chamber according to standard methods of measurement. The collection cell is purged of the initial set-up fluid. The sample fluid is then pumped through the artificial capillary so that the oxygen can diffuse through the capillary wall, and the sample is collected in the a gas-tight withdrawal syringe. The removed sample is tested using a blood gas analyzer or any other electrode system to measure $PO_2$, $PCO_2$, and pH. Total oxygen present in the fluid and transferred out of the capillary is calculated as a function of the diffusion constants for $O_2$ and $HbO_2$, the difference in partial $O_2$ pressure inside and outside the capillary, the gradient of hemoglobin saturation from the center of the capillary to its walls, the cross-sectional area of the capillary, the flow rate, and the distribution of oxygen between free- and chemically-bound states.

An empirical diffusion constant is calculated as a function of the diffusion in $O_2$ partial pressure at the capillary, the Hb concentration, the flow rate, the known OEC of the sample and the cross-sectional area and length of the capillary. Alternatively, if the diffusion constant of the sample is known, the OEC can be calculated.

BRIEF DESCRIPTION OF DRAWINGS

Understanding of the present invention will be facilitated by consideration of the following detailed description of a preferred embodiment of the present invention taken in conjunction with the accompanying drawings, in which like numerals refer to like parts and in which.

DETAILED DESCRIPTION OF PREFERRED EMBODIMENT

The preferred embodiment herein is described in its application to measurement of oxygen transport in a hemoglobin-based blood substitute (HBOC). The applications of the inventive system and method are not intended to be limited to the exemplary application to oxygen transport in HBOCs, but include use in measurements of gas transport properties in other fluids, for example, natural blood and blood products, fuels, or liquid polymers, and the transport of oxygen or other gases, for example, carbon dioxide, carbon monoxide, or nitric oxide.

Figure 1:
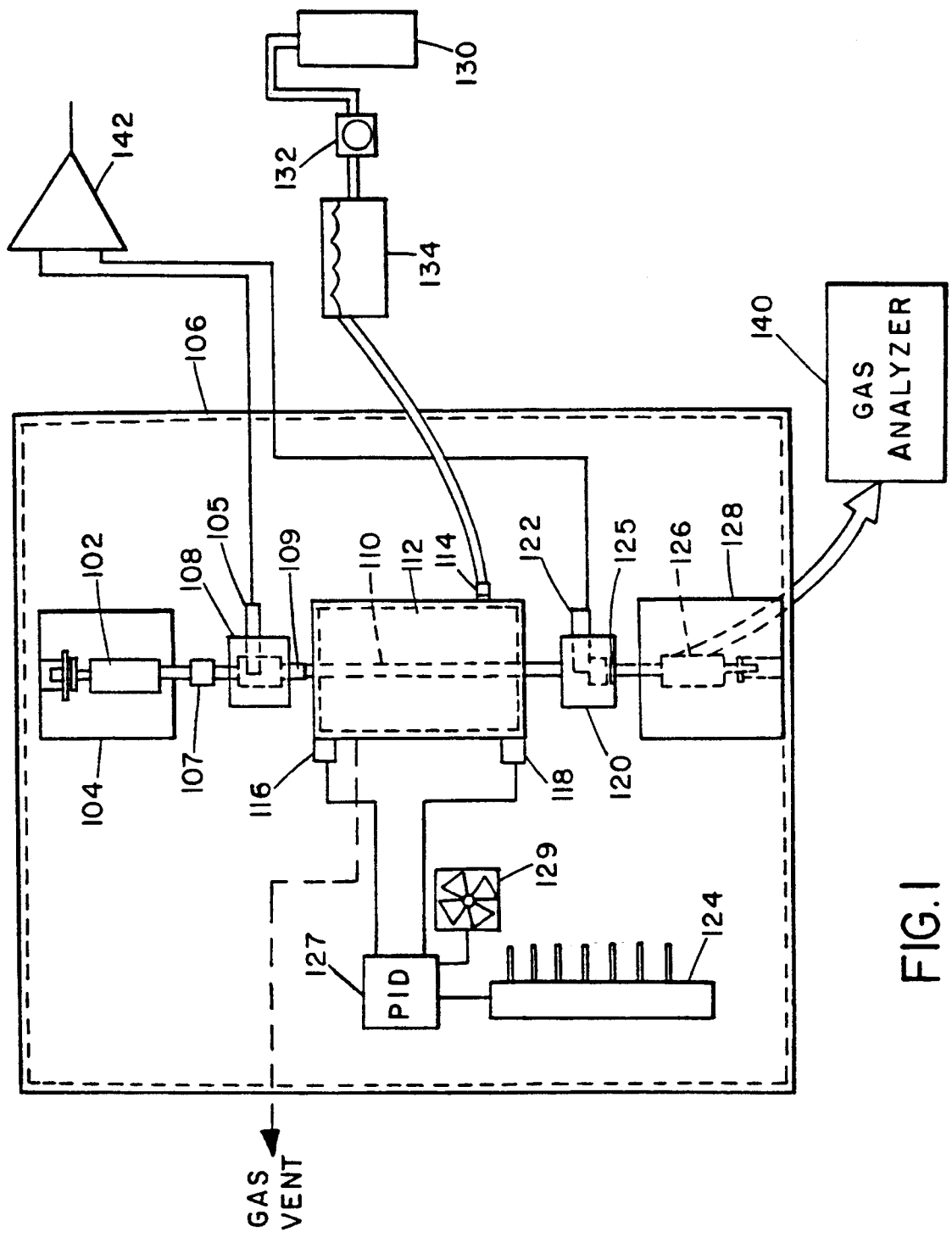
FIG. 1 is a diagram of the artificial capillary system.
Figure 9:
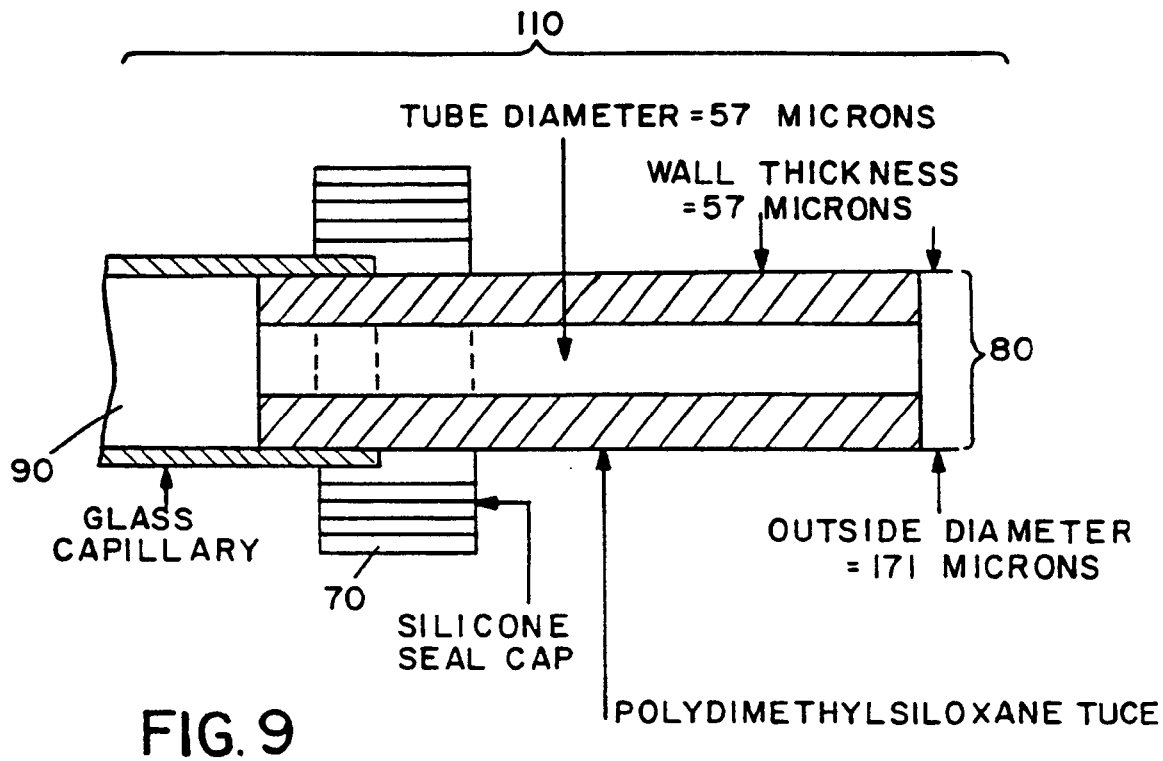
FIG. 9 is a diagrammatic sectional view of the detailed structure of the artificial capillary.

FIG. 1 provides a block diagram of an exemplary artificial capillary testing apparatus (ACTA) of the present invention. The ACTA combined with the analytical instruments described herein comprise the system of the present invention. Artificial capillary 110, shown in detail in FIG. 9, is a tube with a wall thickness approximately equal to its diameter (57 $\mu$m) and is formed from a thin hollow silicone fiber 80. At the upper or entrance end of the silicone tube 80, a glass capillary 90 provides connection for introduction of the fluid into silicone tube 80. The diameter of tube 80 is as small as can be manufactured while still retaining its structural integrity. However, given that a red blood cell is approximately 8 $\mu$m in diameter, tube 80 is capable of approximating the scale on which gas transport occurs in vivo. The silicone tube 80 is manufactured by Point Medical Corporation of Crown Point, Ind. by way of an extrusion process using polydimethylsiloxane (Silastic™). Glass capillary 90 is manufactured by Drummond Scientific (Broomall, Pa.) as a 2 $\mu$l Microcap pipette. The seal between the glass 90 and silicone 80 tubes is provided by seal cap 70, formed using RTV 60 silicone, which is available from General Electric.

A typical length of silicone tube 80 is 100 mm, based on the determination that an artificial capillary tube volume having the selected dimensions will produce residence times that are similar on a physiological scale to typical in vivo capillary transit times, which are 0.37–1.5 seconds for the artificial capillary and 0.75 seconds for an in vivo capillary.

Referring again to FIG. 1, infusion syringe pump 104 obtained from KD Scientific of Boston, Mass., which includes gas tight syringe 102, is connected to entry oxygen flow cell 108 by a short piece of low-permeability Tygon® tubing 107. Oxygen probe 105 is provided within entry oxygen flow cell 108 and may be one or more Clark-type electrodes, which are available from Instech, Plymouth Meeting, Pa. Oxygen probe 105 is primarily intended for monitoring of the system, particularly to confirm the removal of oxygen from the exchange chamber 112, but can be used for data collection, if desired, however, in most circumstances, data is obtained using blood gas analyzer 140. Where probe 105 is included for collection, probe 105 can be omitted if the sample being tested has a known or pre-calculated oxygen content. The exit port of oxygen flow cell 108 is connected to another short piece of Tygon® tubing 109, which, in turn, is firmly attached to glass capillary 90 of artificial capillary 110 using a micro-tube connector (Cole-Parmer, Niles, Ill.). Artificial capillary 110 is encased in gas-tight exchange chamber 112, made of clear acrylic, plastic or other suitable non-permeable material. Bimetallic temperature probes 116, 118 (YSI 700, Yellow Springs, Ohio) are attached near the entry and exit points of fluid flow in exchange chamber 112 for monitoring to ensure that the desired 37° C. is maintained. During testing, the environment within gas-tight exchange chamber 112 is filled with pure nitrogen flowing at a constant rate to replace the gas volume in exchange chamber 112 every 10 seconds. The nitrogen source, preferably at least 99.99% pure, is gas tank 130 with the flow controlled by flow meter 132. The $N_2$ is humidified by bubbling the gas through water bath 134, in which the water is maintained at 37° C. The resulting humidified $N_2$ is delivered by a suitable gas line through the wall of cabinet 106 and through gas inlet 114 into chamber 112. The circulating nitrogen gas is vented out of chamber 112 and cabinet 106, as indicated by dashed lines.

The present invention is not limited to the use of nitrogen as the exchange gas, nor is it limited to diffusion out of the capillary, but can include gas uptake measurements as well. For example, the exchange gas can be a nitrogen/carbon dioxide mixture, and a blood or blood substitute sample can be measured for uptake of $CO_2$. As will be apparent to those in the art, other exchange gases may be used.

The temperature within cabinet 106 is maintained at 37° C. during the procedure through the use of fin heater 124, fan 129 and PID (Proportional, Integral, Derivative) controller 127 for automatic adjustment in response to measurements by temperature probes 116, 118. Note that it is not necessary for PID controller 127 to be located within cabinet 106, but is merely illustrated within the cabinet for convenience, Generally, in order to avoid the influence of electronic components on the temperature within cabinet 106, most, if not all electronic components will be located outside of cabinet 106. Cabinet 106 is openable to permit access for insertion and removal of gas-tight syringes 102 and 126, but should be sufficiently sealable to minimize temperature fluctuations caused by loss of warmed air or by cooler air introduced from outside the cabinet. The power source (not shown) for driving each of the electronic components of the apparatus will be a conventional voltage supply, the selection of which will be apparent to those in the art.

Collection cell 120 is mated directly with the end of artificial capillary 110 using RTV silicone sealant and a polypropylene microfitting. Collection cell 120 is formed from a solid piece of acrylic or other inert material and can include a T-shaped splitter to permit diversion of small amounts of the fluid to an optional flow meter or insertion of a second oxygen electrode 122, which is preferably identical to electrode 105. If a flow meter is utilized, the flow meter is preferably a calibrated measuring tube which feeds back into a port in collection cell 120. If oxygen electrodes are included, the outputs of oxygen electrodes 122 and 105 can both be input to differential amplifier 142 which can provide a differential output to a readout device (not shown) or to a processor (not shown) to indicate and/or calculate the differential oxygen content of the fluid upstream and downstream of artificial capillary 110. Collection cell 120 can include a stirring device, such as a magnetic stirrer, to prevent the formation of any dead space within the cavity arising from changes in volume, which can effect measurement by electrode 122.

As is known in the art, other devices are known for measurement of oxygen level and may be substituted for oxygen electrodes 105 and/or 122. For example, optical cells can be inserted into the apparatus both upstream and downstream of artificial capillary 110, at or near flow cell 108 and collection cell 120. A light source, either monochromatic or polychromatic, can be located near the optical cell, or the light can be conducted from a light source located outside of cabinet 106 using an optical fiber or light pipe in order to avoid introduction of a potential heat source in the cabinet. A monochrometer is located on the side of the optical cell opposite the point of introduction of the light. In the case of hemoglobin, the monochrometer is set at an appropriate wavelength, as is known in the art. The wavelength will vary based upon the gas or other material of interest, the fluid density (viscosity), and other factors. The change in gaseous ligand state which occurs as the fluid passes through artificial capillary 110 will result in a change in optical absorbance. For example, it is known that for measurement of deoxygenation in normal blood, wavelengths of 560 nm is the wavelength of maximum absorbance. The absorbance measurements can be displayed on a readout device, or can be input to a processor for calculation and/or comparison to, or correlation with, other detected parameters. The described optical example and similar optical analytical techniques, as well as other techniques, such as acoustic measurement techniques, are known in the art and can be readily implemented in conjunction with the present invention.

The combined length of exchange chamber 112 and collection cell 120 is approximately 25.4 cm (10 in.). A gas-tight septum 125 seals the exit end of collection cell 120. Second gas-tight syringe 126 pierces gas-tight septum 125 and collects the sample as syringe pump 128 slowly draws fluid at a rate slower than the flow rate to prevent the creation of voids within the fluid. The effluent fluid collected in syringe 126 is removed from syringe pump 128 for analysis to determine gas content using blood gas analyzer 140. In the test system, a type ABL-5 analyzer from Radiometer America, Inc. of Westlake, Ohio was used.

As viscosity measurements are helpful in evaluation of the fluids, as discussed below with regard to the inventive method, the ACTA can be modified to measure the viscosity of the fluid under test by replacing the silicone tube 80 of artificial capillary 110 with a non-flexible material, such as glass. Optional flowmeters or pressure transducers can be located upstream from the artificial capillary 110, e.g., at location 109, and downstream, e.g., at or prior to collection cell 120. The change in flowrate or the pressure drop across the glass capillary of known radius permits determination of the fluid's viscosity.

The above-identified materials and components, and the specified sources, are intended to be exemplary only. It will be apparent to those skilled in the art that the specific materials and components of which the apparatus is formed, and the identified sources, are provided as examples only, and other suitable materials from other sources may be substituted to produce like results.

The ACTA provides means for exploring the processes of absorption/desorption, reaction and flow with a solution containing chemically reactive species. The ACTA does not mimic the processes found in the body, but can, nonetheless be used to evaluate hemoglobin-containing solutions to determine the effectiveness of oxygen transport by such solutions. A generalized protocol for usage of the ACTA in evaluation of gas transport in blood and blood substitutes is as follows:

1) the ACTA is assembled in an air environment at 37° C.;
2) samples are conditioned in a tonometer (ISL 2000) to a gas pressure with ~150 mmHg oxygen and o mmHg carbon dioxide;
3) samples are aspirated into a gas tight syringe and placed onto a syringe pump;
4) flow is established at a specific resident time;
5) the gas environment in the exchange chamber is changed from air to the exchange gas (nitrogen or nitrogen-carbon dioxide)
6) samples are collected by withdrawal syringe pump into a gas-tight syringe;
7) gas pressure and pH level are evaluated with a blood gas analyzer.

The ACTA is designed as a steady-state system; real time measurements of transport are not obtained. The ACTA measures the overall diffusional transport for a given flow rate after exchange has taken place. The difference in the gas pressure levels before and after the exchange chamber is the fundamental measurement.

Using the above-described system, in an exemplary method of the present invention, several cell-free hemoglobin solutions and a red blood cell (RBC) suspension were evaluated. The hemoglobin concentration (in heme) used for all test solutions was 3 mM. It should be noted that the inventive method is not intended to be limited to this concentration, and other concentrations may be used. Concentrations for the hemoglobin solutions were determined by visible spectrophotometry using a Milton Roy 300 Diode Array Spectrophotometer, available from Spectronics Instruments, Inc., Rochester, N.Y., with evaluation using extinction at 523 nm (E=7.12 mM$^{-1}$cm$^{-1}$). The hemoglobin concentration for RBCs was determined using a technique in which the cells are lysed, and the hemoglobin was converted to azomethoglobin for spectral determination of concentration.

The oxygen equilibrium curves (OEC) for the hemoglobin samples were measured using charge-coupled diode array spectrophotometry with catalytic deoxygenation of oxyhemoglobin. Oxygen binding curves were determined for RBC suspensions using methods known in the art. Adair constants were fitted from the measured equilibrium curves using least-squares minimization routines. Solution properties, including colloid pressure (COP) and viscosity ($\eta$), were measured for each sample.

In the exemplary method of the present invention, the test solutions were equilibrated with humidified air in a tonometer in accordance with known procedures for blood gas analysis. The partial pressure of oxygen (PO$_2$) was calculated using the barometric pressure on the day of each of the experiments less the water vapor pressure at the temperature (37° C.) at which each experiment was run. Referring again to FIG. 1, the samples were transferred using gas-tight syringe 102 to infusion syringe pump 104. Flow was established throughout the system at three selected flow rates, 10, 20, and 40 $\mu$l/min, which were chosen to give residence times in capillary 110 of 1.56, 0.75, and 0.39 seconds, respectively.

The test solution was first delivered through capillary 110 in an air-equilibrated environment in order to establish equal PO$_2$ at both entry and exit points. Once equal air partial oxygen pressures were achieved, the gas environment outside of capillary 110 and within gas-tight exchange chamber 112, was switched to pure nitrogen at a constant rate of gas flow to replace the volume of gas in exchange chamber 112 every 10 seconds. The incoming nitrogen gas was humidified and maintained at a temperature of 37° C. Oxygen electrodes 108, 122 were used to evaluate the gas composition in exchange chamber 112. Over 95% of the oxygen was removed from exchange chamber 112 within the first minute and, after 2 minutes, no oxygen could be detected. A five minute delay period from the start of gas flow to the start of sample collection was allowed to ensure that the interior of exchange chamber 112 contained only the exchange gas, and that residual fluid in collection cell 120 had been fully purged.

The sample collected at the exit port into withdrawal syringe 126 was analyzed using blood gas analyzer 140 to determine PO$_2$, PCO$_2$, and pH in the effluent sample. A minimum of three samples were taken at each of the different flow rates to ensure steady-state conditions and to establish a range of values for a given residence time.

In the case of normally operating biological systems, when cell-free hemoglobin is present, the transport (flux, $-J$) of oxygen through a vessel wall is calculated as the sum of the diffusion of free- and chemically-bound oxygen or HbO$_2$. Then:

$$-J = \frac{D_{O2}\Delta O_2}{\Delta x} + \frac{D_{HbO2}\Delta Y[Hb]_T}{\Delta x} \qquad (1)$$

where:

$D_{O2}$ and $D_{HbO2}$ are the diffusion constants for O$_2$ and HbO$_2$, respectively;

$\Delta O_2$ is the difference in partial pressure of O$_2$ inside and outside the vessel;

$\Delta x$ is the effective wall thickness of the capillary;

$\Delta Y$ is the gradient of hemoglobin saturation from the center of the vessel to its wall; and $[Hb]_T$ is the total cell-free hemoglobin concentration.

Equation 1 is derived from Fick's first law, which provides that the flux ($-J$) through the silicone capillary is equal to a diffusion coefficient (D) times a concentration gradient $-J=D(dC/dx)$. The right hand side of the equation can be separated into a concentration difference times a mass transfer coefficient, $\kappa$, which has units of cm/sec. The $\kappa$ combines the diffusion coefficient with the distance factor dx and is characterized in terms of the rate of diffusion across an area normal to the interface. The solubility of a gas within the silicone capillary follows Henry's Law, P=HC, where P is the applied gas pressure (in atm.), H is Henry's constant in vol-atm/mol, and C is the concentration of the solvated gas in liquid, in mol/vol.

The diffusivity of O$_2$ ($D_{O2}$) is well known in the art and has been measured as a function of hemoglobin concentration. However, the O$_2$ flux ($-J$) in a hemoglobin solution is augmented by its chemical reactivity with hemoglobin. Because the majority of O$_2$ in saturated oxyhemoglobin solutions is carried as chemically bound HbO$_2$, the diffusivity of O$_2$ is facilitated by the diffusion of HbO$_2$. Diffusion constants for HbO$_2$ ($D_{HbO2}$) as a function of hemoglobin concentration have been reported. The diffusivity of HbO$_2$ is a function of viscosity and molecular radius, as defined by the Stokes-Einstein equation:

$$D_{HbO2} = \frac{kT}{6\eta_a r_b} \quad \text{For } r_b \gg r_a \qquad (2)$$

where:

k is Boltzman's constant;

$\eta_a$ is the viscosity of the solvent (i.e., water);

$r_b$ is the radius of the solute (i.e., $HbO_2$);

and $r_a$ is the radius of the solvent molecules.

For molecular oxygen, where molecular radius (rb) is approximately the same as the solvent ($H_2O$), the Stokes-Einstein equation becomes:

$$D_{O2} = \frac{kT}{4\eta_a r_b} \quad \text{For } r_b \approx r_a \tag{3}$$

Thus, for both $HbO_2$ and dissolved $O_2$, the diffusivities are inversely related to the viscosity of the macromolecular solutions (Equations 2 and 3). For cell-free hemoglobin, hemoglobin molecular size is an additional factor in that $D_{HBO2}$ is inversely proportional to the molecular size of hemoglobin ($r_b$ in Equation 2). This analysis predicts potential strategies to reduce or eliminate facilitated diffusion by cell-free hemoglobin by increasing molecular radius and solution viscosity.

Further analysis of the Equation 1 provides an understanding of an additional strategy to defeat the mechanisms of facilitated diffusion. The gradient along which $HbO_2$ diffuses is $[Hb]_T \Delta Y$ and the distance through which $HbO_2$ must diffuse is $(\Delta X_{HbO2})$. The quantity $\Delta Y$ at a given $PO_2$ is the slope of the oxygen equilibrium curve at that $PO_2$, and is dependent on the shape of the curve (a property of the hemoglobin molecule) and its position (i.e., P50).

To summarize, the total $O_2$ transferred in a cylindrical section of the artificial capillary can be described as follows:

$$\Delta O_{2T} = \frac{\pi x^2}{R} \times \left[ \frac{D_{O2}\alpha \Delta PO_2}{\Delta X_{O2}} + \frac{D_{HbO2}[Hb]_T \Delta Y}{\Delta X_{HbO2}} \right] \tag{4}$$

where:

x is the radius of the capillary;

R is the flow rate.

Equation 4 shows the contribution of $HbO_2$ diffusion to total $O_2$ transport. This form of the $O_2$ transfer equation has an interesting property in that it shows the contribution of the $HbO_2$ diffusion to be dependent on 4 variables:

For each segment of distance along the capillary, the total $O_2$ present in the solution is:

$D_{HbO2}$ is the diffusion constant for $HbO_2$;

$[Hb]_T$ is the total hemoglobin concentration;

$\Delta Y$ is the difference in hemoglobin saturation between each radial increment $\Delta x$ of the capillary;

$\Delta X_{O2}$ is the incremental distance for diffusion of $O_2$; and $\Delta X_{HbO2}$ is the incremental distance for diffusion of $HbO_2$.

Equation 4 reveals a number of strategies that can be employed independently or in combination to modulate $O_2$ transfer ($\Delta O_{2T}$). The strategies are defined by the relationship of $\Delta O_{2T}$ to the alterable Solution properties, such that $\Delta O_{2T}$ is:

(1) inversely proportional to solution viscosity ($\eta$), according to Equations 2 and 3, through changes in both $D_{O2}$ and $D_{HbO2}$;

(2) inversely proportional to molecular size ($r_{HbO2}$), according to Equation 2 through a change in $D_{Hbo2}$;

(3) directly proportional to $[Hb]_T$; and (4) directly proportional to $\Delta Y$ ($\Delta Y$ can be altered by changing O2 affinity and/or cooperativity of $O_2$ binding).

To minimize the effects of facilitated diffusion on $\Delta O_{2T}$ from cell-free hemoglobin-based oxygen carriers, a given $\Delta O_{2T}$ based on the value for red blood cells can be achieved using the above strategies independently or in combination.

For each segment of distance along the capillary, the total $O_2$ present in the solution is:

$$O_{2T} = \alpha PO_2 + Y[Hb]_T \tag{5}$$

where:

α is the solubility coefficient of $O_2$ in plasma (1.210μM/Torr);

Y is hemoglobin saturation; and $[Hb]_T$ is total hemoglobin concentration.

The amount of $O_2$ transferred out of the capillary in the segment dx is:

$$\Delta O_2 = \frac{K * (\Delta PO_2)(\pi r^2) dx}{R} \tag{6}$$

where:

K* is a lumped diffusion parameter, consisting of the diffusion constants given in Equation 1 and the length of the diffusion gradient for $O_2$;

$\Delta PO_2$ is the $PO_2$ gradient (essentially the interior $PO_2$ when $N_2$ is the outside gas);

r is the radius of the capillary; and

R is the flow rate.

Total $O_2$ is now designated as $\Delta O_2$. At this point, the Adair equation, using the known OEC parameters for the hemoglobin in question, is used to empirically find the $PO_2$ and Y combination to provide the new $O_{2T}$ according to Equation 5. The measurement process is repeated until the fluid sample reaches the end of the capillary, and the final $PO_2$ is matched with the value actually measured in the experiment.

The analysis of oxygen transport using the ACTA requires attention to three essential properties of a hemoglobin solution; 1) the solution medium; 2) the capacity of the hemoglobin solution for binding oxygen; which includes the hemoglobin concentration as well as its purity; 3) the shape of the OEC; whether the curve is shifted right (low affinity) or shifted left (high affinity) of unmodified, normal hemoglobin will influence the amount of oxygen that is delivered over a given $PO_2$ range. Aqueous plasma represents the intermediate condition between the gas phase outside the artificial capillary and oxygen that is bound to the hemoglobin. The properties of this fluid will influence the diffusion of gases.

For the evaluation of diffusion properties, the oxygen carrying capacities of the hemoglobin solutions should be evaluated. A simple aqueous medium, such as a solution of Bis-tris (2,2-bis(hydroxymethyl)-2,2',2"-nitrolotriethanol), can be used to establish a base-line level for oxygen contained within solution. At 37° C., and 150 mm Hg, the simple aqueous medium has an oxygen concentration of around 180 μM. With no hemoglobin in this solution, there is no reserve capacity for oxygen binding, i.e., oxygen can be easily removed from this solution. When hemoglobin is added to the solution, a reserve capacity for oxygen binding is created.

As previously stated, the typical concentration of hemoglobin used in the method of the present invention is around 3 mM. At this concentration, each heme group binds one to one with oxygen, i.e., a 3 mM solution of hemoglobin at 150 mmHg (e.g. 100% saturation) will contain 3 mM of oxygen in addition to the oxygen already contained within the simple aqueous medium (180 μM or 0.18 mM). Therefore, the total capacity for oxygen transport of the hemoglobin solution is increased to approximately 3,200 μM compared with 180 μM for the simple aqueous solution.

In addition to altered reserve capacity, any given hemoglobin will have a uniquely shaped OEC. A curve that is positioned on the right side is said to have a low affinity for hemoglobin because such a curve indicates that the hemoglobin will release it's oxygen at a higher partial pressure compared with a hemoglobin that is shifted left. The P50 is used as a general index of oxygen affinity. A low P50 indicates the OEC is shifted to the left representing a high oxygen affinity. A high P50 indicates a hemoglobin with a lower oxygen affinity and will therefore release it's oxygen more readily.

The shape of the OEC is important, particularly the slope of the curve for a given range of $PO_2$. Curves with a shallow slope generally indicate a hemoglobin with low oxygen affinity. The slope of the curve will also indicate any effects on the manner in which oxygen is transported and delivered. A hemoglobin solution which produces a shallow curve will release oxygen in a steady, continuous fashion. A steep curve represents large amounts of oxygen being released over a short range of oxygen pressure.

obtained from healthy volunteers and washed three times with normal saline to remove the plasma and buffy coat.

The hemoglobin concentration (in heme) used for all test solutions was 3 mM. Concentrations for the hemoglobin solutions were determined by visible spectrophotometry using the extinction at 523 nm. The hemoglobin concentration for RBCs was determined using a technique in which the cells are lysed, and the hemoglobin in converted to azomethoglobin for spectral determination of concentration. It was determined that the percentage of methemoglobin in each sample was less than 2–4%.

Figure 2:
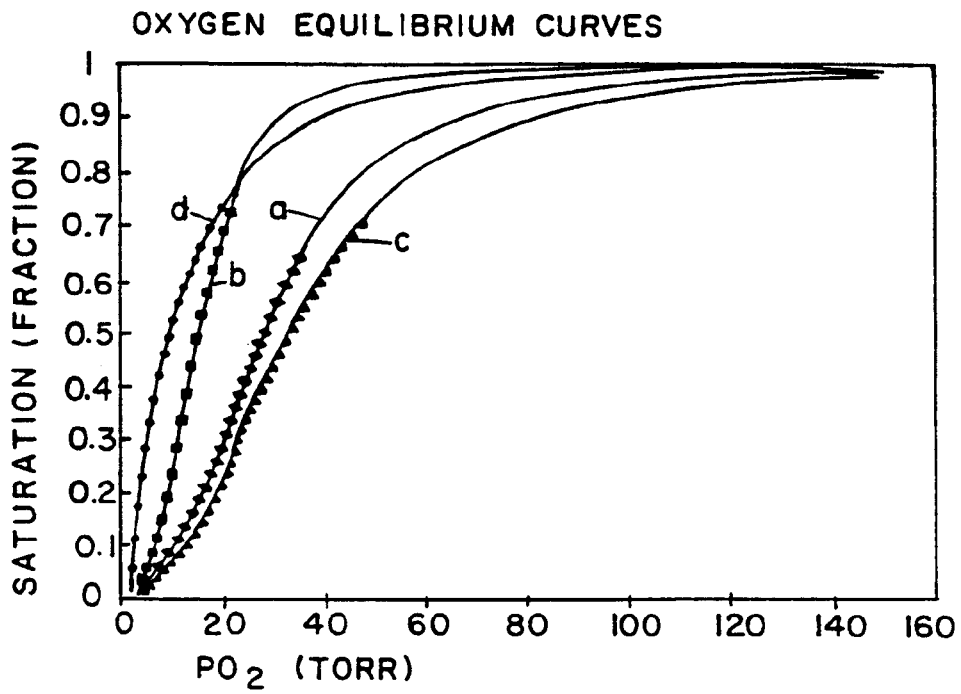
FIG. 2 is a plot of oxygen equilibrium curves of the exemplary hemoglobins studied.

Oxygen equilibrium curves for the hemoglobin samples were measured using coupled diode array spectrophotometry and are shown in FIG. 2. The Adair parameters, P50 and Hill coefficients are provided in Table 1, which summarizes the physical properties of hemoglobin solutions used in the experiment.

TABLE 1

|  | RBC | $HbA_o$ | PEG-Hb | $\alpha\alpha$-Hb |
| --- | --- | --- | --- | --- |
| $a_1$ | $1.48 \times 10^{-2}$ | $4.01 \pm 0.82 \times 10^{-2}$ | $1.47 \pm 0.39 \times 10^{-1}$ | $2.22 \pm 0.26 \times 10^{-2}$ |
| $a_2$ | $8.53 \times 10^{-4}$ | $1.74 \pm 0.44 \times 10^{-3}$ | $4.27 \pm 0.20 \times 10^{-3}$ | $9.51 \pm 0.19 \times 10^{-4}$ |
| $a_3$ | $4.95 \times 10^{-8}$ | $5.95 \pm 5.95 \times 10^{-13}$ | $2.43 \pm 1.91 \times 10^{-4}$ | $1.34 \pm 0.69 \times 10^{-11}$ |
| $a_4$ | $1.07 \times 10^{-6}$ | $2.48 \pm 0.57 \times 10^{-5}$ | $1.48 \pm 0.13 \times 10^{-4}$ | $1.05 \pm 0.13 \times 10^{-6}$ |
| P50 | 32.8 | 15.1 | 10.2 | 33.8 |
| n | 2.59 | 2.97 | 1.38 | 2.43 |
| viscosity (cp) | — | 0.9 | 3.2 | 0.9 |
| COP (mm Hg) | — | 16.4 | 118.0 | 16.2 |
| radius (Å) | — | 64 | 282 | 62 |
| [Hb], mM | 3.05 | 3.05 | 2.50 | 3.03 |

The goal in the original design of HBOCs was to simulate the OEC blood. Theoretically, regardless of the modifiers that affect human hemoglobin $A_O$, by designing an OEC is similar to the OEC of whole blood, the transport of oxygen should be roughly the same within a given range of $PO_2$. Of fundamental importance with regard to HBOCs is the precise delivery of oxygen to the tissues in correct amounts. In vivo, oxygen delivery is regulated by vasoactive metabolites that respond to changes in oxygen levels such that flow is adjusted to reflect the needs of the tissues. Too much oxygen is toxic to the tissue, too little oxygen leads to suffocation. Active vasocontrol by the arterioles regulate blood flow so as to adjust oxygen pressure as needed. As such, an HBOC that mimics the delivery processes of blood most correctly would avoid over or under stimulation of these vasoactive metabolites and other biological processes that may effect oxygen delivery.

The following example provides an illustration of the application and method of the present invention to evaluate and characterize the gas transport properties of cell-free hemoglobins.

EXAMPLE 1

Oxygen in Hemoglobin Solution

Three cell-free hemoglobin solutions and a red blood cell suspension were evaluated. The cell-free systems included: 1) purified human hemoglobin $A_O$ ($HbA_O$, Hemosol, Inc.); 2) human hemoglobin cross-linked using 3,5-dibromosalicyl fumerate, which provides a covalent attachment between $\alpha Lys99$ residues ($\alpha\alpha$-Hb, Blood Research Detachment, Walter Reed Army Institute for Research); and 3)bovine hemoglobin conjugated at its surface to polyethylene glycol (PEG-Hb, Enzon). The PEG-Hb has an approximate molecular weight of 5000 Da. Human red blood cells were Under the test conditions, the binding curve for $\alpha\alpha$-Hb (c) is shifted slightly to the right of the RBC curve (a), while the $HbA_O$ (b) and PEG-Hb (d) curves are shifted substantially to the left of the RBC's (a), as shown in FIG. 2. The RBC (a), $\alpha\alpha$-Hb (c), and $HbA_O$ (b) curves are all highly cooperative with ($n \geq 2.4$). The PEG-Hb (d) curve exhibits much less cooperativity (n=1.4).

Figure 3:
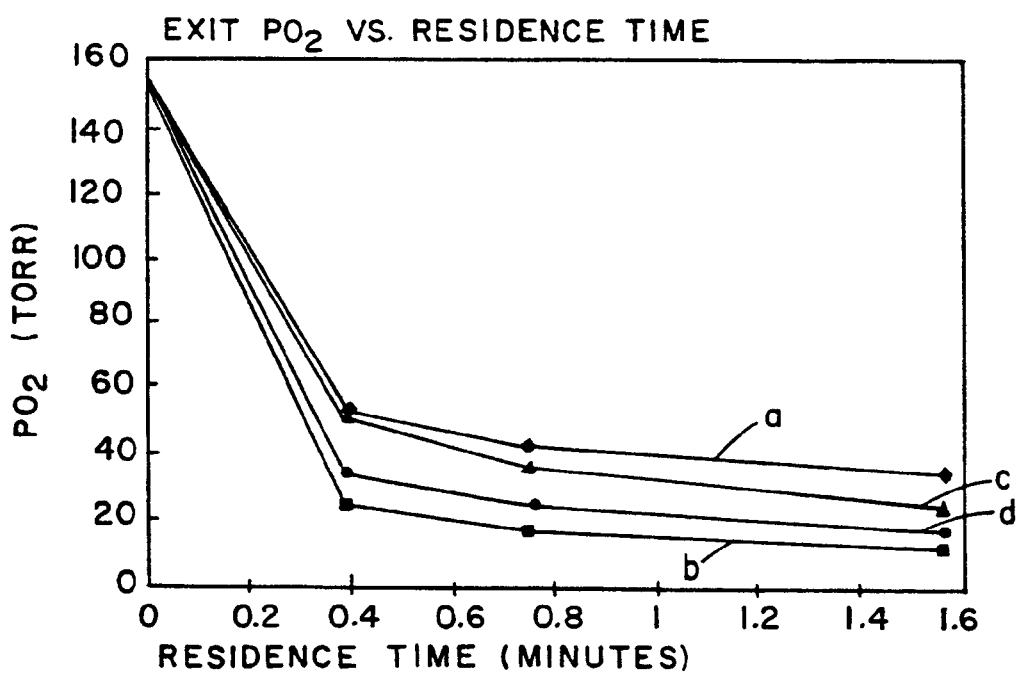
FIG. 3 is a plot of exit $PO_2$ measurements as a function of residence time in the artificial capillary at a given flow rate.

Exit $PO_2$ values versus residence times are provided in FIG. 3. At any given flow rate, the lowest exit value is seen for $HbA_O$ (b) followed by PEG-Hb (d), $\alpha\alpha$-Hb (c), and RBCs (a) with the highest exit $PO_2$ values.

Assuming equilibrium and using the same exit $PO_2$ values, the final fractional saturation of hemoglobin in the artificial capillary was calculated from the Adair constants given in Table 1. The calculated fractional saturations for each sample as a function of residence time are provided in FIG. 4. PEG-Hb (d) showed the least desaturation over time at any flow rate, which was closely paralleled by the RBC (a) profile. $HbA_O$ (b) and $\alpha\alpha$-Hb (c) both showed much greater degrees of desaturation. Capillary oxygenation parameters of the solutions are provided in Table 2.

TABLE 2

| Flow ($\mu$l/min) | Residence Time (seconds) | $PO_2$ (mm Hg) | K* ($\mu$M/min mm Hg) | Saturation (fraction) |
| --- | --- | --- | --- | --- |
| RBC | | | | |
| 0 | 0 | 152 | — | 0.986 |
| 10 | 1.56 | 34 | 887 | 0.612 |
| 20 | 0.75 | 42 | 1032 | 0.734 |
| 40 | 0.39 | 53 | 1086 | 0.836 |

TABLE 2-continued

| Flow ($\mu$l/min) | Residence Time (seconds) | $PO_2$ (mm Hg) | K* ($\mu$M/min mm Hg) | Saturation (fraction) |
|---|---|---|---|---|
| $HbA_O$ | | | | |
| 0 | 0 | 152 | — | 0.990 |
| 10 | 1.56 | 11 | 4301 | 0.287 |
| 20 | 0.75 | 17 | 3838 | 0.581 |
| 40 | 0.39 | 25 | 2564 | 0.820 |
| $\alpha\alpha$-Hb | | | | |
| 0 | 0 | 152 | — | 0.998 |
| 10 | 1.56 | 24 | 1772 | 0.321 |
| 20 | 0.75 | 36 | 1826 | 0.551 |
| 40 | 0.39 | 51 | 1591 | 0.747 |
| PEG-Hb | | | | |
| 0 | 0 | 152 | — | 0.998 |
| 10 | 1.56 | 16 | 1209 | 0.660 |
| 20 | 0.75 | 24 | 1120 | 0.794 |
| 40 | 0.39 | 34 | 1076 | 0.878 |

Figure 4:
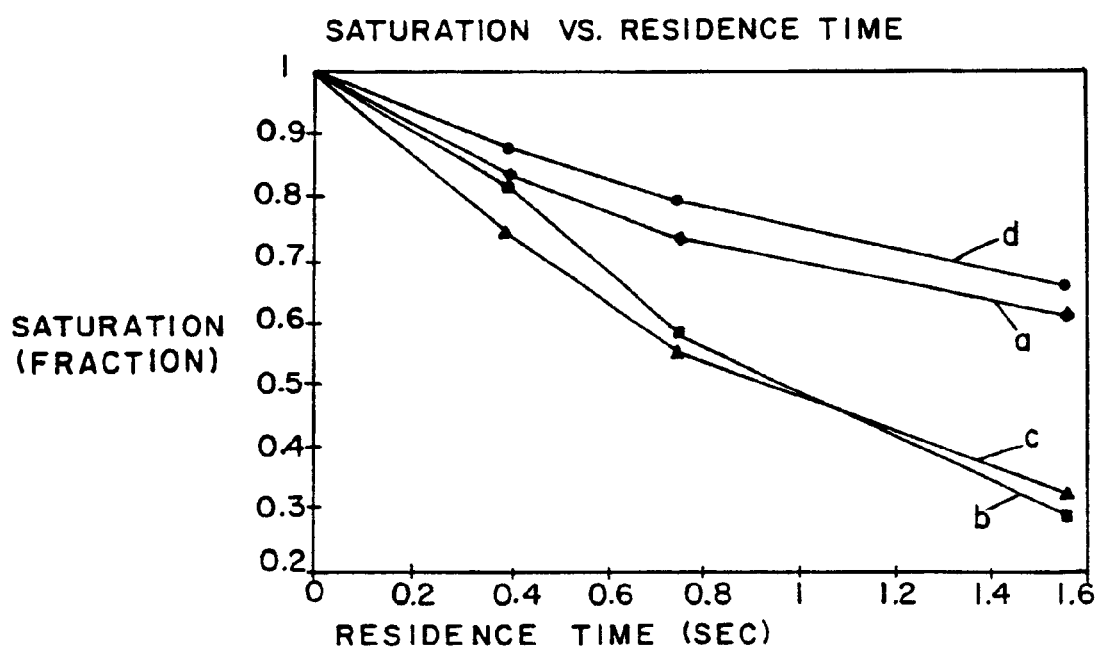
FIG. 4 is a plot illustrating hemoglobin saturation as a function of residence time in the artificial capillary system.
Figure 5:
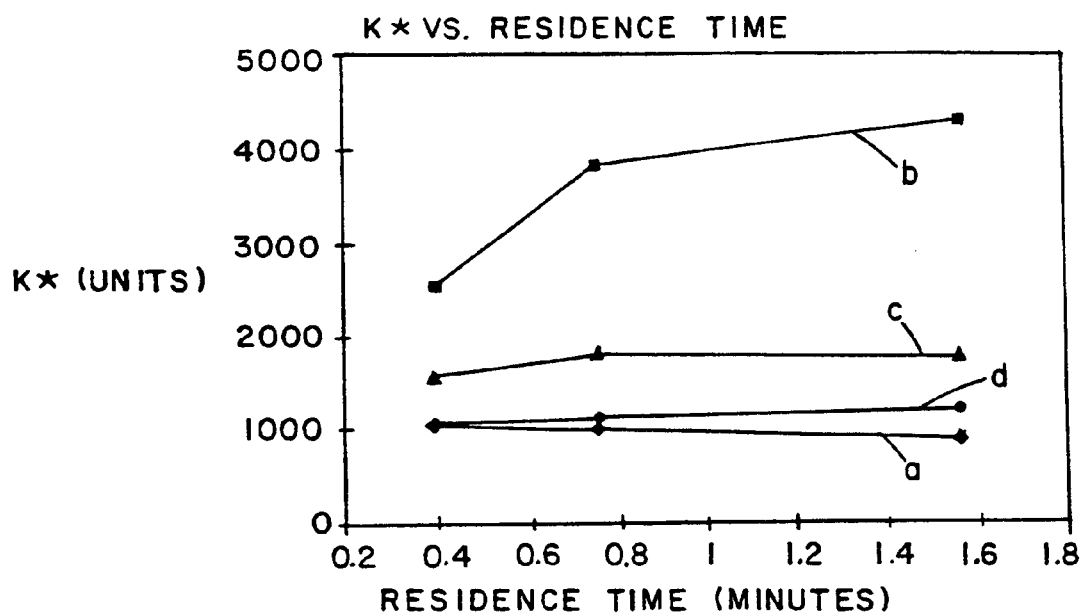
FIG. 5 is a plot of the calculated combinatorial diffusion constant, K*, as a function of the residence time in the artificial capillary system.

The differences in desaturation can also be inferred by comparing saturation versus residence time for the oxygen carrying samples shown in FIG. 4. $\alpha\alpha$-Hb (c) and RBC (a) hemoglobin have similar oxygen equilibrium curves FIG. 2), but $\alpha\alpha$-Hb (c) shows a greater degree of desaturation down the capillary due to the absence of intraluminal forces that resist the diffusion of $O_2$ out of RBCs and to the facilitated diffusion of cell-free $HbO_2$, thereby giving a higher K* value for $\alpha\alpha$-Hb (c) compared with RBCs (a), 1800 vs. 1000, shown in FIG. 5. $\alpha\alpha$-Hb (c), $HbA_O$ (b), and PEG-Hb (d) are all cell-free $O_2$ carriers that theoretically will enhance $O_2$ transport by the facilitated diffusion Of $O_2$ through the diffusion of $HbO_2$. In this case, $\alpha\alpha$-Hb and $HbA_O$ will present the same $D_{HBO2}$ values due to the similarity in their size and solution viscosity, and their fractional saturations at the exit of the capillary are similar. However, FIG. 5 shows that the fitted value of K* for the $HbA_O$ solution (b) is higher compared with $\alpha\alpha$-Hb (c), 3800 versus 1800, respectively, at a flow rate of 20 $\mu$l/min, due to the high $O_2$ affinity of $HbA_O$ and the steep $HbO_2$ gradients once it begins to desaturate during its transit down the capillary. In contrast, $D_{HbO2}$ for PEG-Hb will be smaller due to the larger size of the PEG-Hb molecule and the higher viscosity of the PEG-Hb solution (see Equation 2). Similarly, the value of $D_{O2}$ will be lower due to higher viscosity (see Equation 3). The net result is that the fitted value of K* for PEG-Hb (d), 1100, at 20 $\mu$l/min as shown in FIG. 5, is lower than for either of the other cell-free solutions studied here and is closer in value to that for the RBC (a) suspension (1000). 3) Considering molecular size and viscosity alone, $D_{HBO2}$ for PEG-Hb should be decreased by a factor of 16. The fact that this decrease is not reflected in K*, which is decreased by a factor of 2–4, is due to the high $O_2$ affinity of the PEG-Hb solution (10 mmHg), and the steep radial gradient. The net result of these factors is still a much lower degree of desaturation for PEG-Hb (d) compared with $HbA_O$ (b) and $\alpha\alpha$-Hb (c), 0.79 vs. 0.58 and 0.55, respectively in FIG. 4.

The finite element analysis adjusts values for the lumped diffusion parameter, K*, until the exit $PO_2$ equals the experimental value. The final fitted values for K* as a function of residence time are shown in FIG. 5 and listed in Table 2. K* was independent of flow rate for RBCs (a), PEG-Hb (d), and $\alpha\alpha$-Hb (c), but increased at slower flow rates for $HbA_O$ (b). At all flow rates, the fitted value was highest for $HbA_O$ (b), which ranged from 2800 to 4300 $\mu$M/min/Torr. Following these values, $\alpha\alpha$-Hb (c) had a value of 1600–1800 $\mu$M/min/Torr. PEG-Hb (d) and RBCs (a) gave similar values for K* from 900–1200 $\mu$M/min/Torr. The various values suggest an order for effective diffusivity of $HbA_O$>$\alpha\alpha$-Hb>PEG-Hb and RBCs. The K* value for $HbA_O$ and $\alpha\alpha$-Hb are higher than for RBCs because of the absence of intraluminal resistances for cell-free solutions. In the cell-free PEG-Hb solution, which has a K* value equal to that for RBCs at the fastest flow rate and which is only slightly higher than RBCs at the slowest flow rate, these effects are negated due to at least two physical properties of the PEG-Hb solution (see Equation 2): (1) higher viscosity compared with tetrameric solutions, and (2) larger molecular size.

FIGS. 6a–6d illustrate calculated profiles of total $O_2$ transport at given entry $PO_2$ at a single point, dx, along artificial capillary 110. Each plot reveals a cross-sectional radius of the capillary at the point dx from the center of the vessel (28.5 $\mu$m) to the outer edge of the vessel (0 $\mu$m), where the $O_2$ exits the vessel. The lines represent the total transport, or flux, of oxygen from the center to the edge of the vessel: RBCs, indicated as line "a", $HbA_O$, shown as curve "b", $\alpha\alpha$-Hb, shown as curve "c"; and PEG-Hb, indicated as curve "d". Transport is represented in units of $cm^2 \cdot mM/sec \cdot km$. Total oxygen transport is calculated as the sum of the two terms in Equation 1, the first for diffusion of free, dissolved oxygen, the second for diffusion of chemically bound $O_2$ as $HbO_2$.

For RBCs, the total flux is calculated solely from the diffusion of dissolved $O_2$, term 1 in Equation 1, since there is no facilitated diffusion term due to cell-free $HbO_2$. Free $O_2$ diffusion is calculated, according to Fick's Law, as the $O_2$ diffusion constant ($D_{O2}$)×the $O_2$ concentration gradient ($\Delta[O_2]/\Delta r$). $\Delta[O_2]=\alpha\Delta PO_2$, where $\alpha$=solubility coefficient for $O_2$ (1.027 $\mu$M/Torr), and $\Delta r$ is equal to the length of the diffusion gradient. The $O_2$ concentration gradient is linear. Therefore, $\Delta PO_2$ is equal to $PO_2$ at the center of the vessel, because the $PO_2$ at the outer edge=0, and $\Delta r$ is simply the radius of the capillary, 28.5 $\mu$m. The values for $D_{O2}$ used in the calculations were $1.96 \times 10^{-5}$ $cm^2$/sec for RBCs, $HbA_O$, and $\alpha\alpha$-Hb. A four-fold lower value, $0.49 \times 10^{-5}$ $cm^2$/sec, was used for PEG-Hb to take into account the four-fold increase in solution viscosity.

The total flux of oxygen for hemoglobin solutions includes the calculations for terms 1 and 2 in Equation 1 due to the added diffusion of $HbO_2$. The diffusion of free $O_2$ is calculated according to Fick's Law, as described in the preceding paragraph. Chemically bound $O_2$ as $HbO_2$ is calculated, according to Fick's Law, as the $HbO_2$ diffusion constant ($D_{HbO2}$)×the $HbO_2$ concentration gradient ($\Delta[HbO_2]/\Delta r$). $\Delta[HbO_2]$ is calculated as $\Delta Y \times [Hb]_{Total}$, the fractional saturation of hemoglobin times the total hemoglobin concentration, and $\Delta r$ is equal to the length of the diffusion gradient. The diffusion for $HbO_2$ is nonlinear as a function of the shape of the oxygen equilibrium curve. Therefore, $\Delta Y \times [Hb]_{Total}$ is calculated in increments of $\Delta r$ in the cross-section of the capillary. The calculations for the plots shown in FIGS. 6a–d used increments of $\Delta r=1/100$th of the vessel radius (0.285 $\mu$m). The values for $D_{HbO2}$ used in these calculations were $2.76 \times 10^{-7}$ $cm^2$/sec for $HbA_O$ and $\alpha\alpha$-Hb. A sixteen-fold lower value, $0.17 \times 10^{-7}$ $cm^2$/sec, was used for PEG-Hb to take into account the four-fold increase in solution viscosity and the four-fold increase in molecular radius.

The pulses in oxygen transport shown for $HbA_O$ (curve b) and $\alpha\alpha$-Hb (curve c), for all entry $PO_2$ values in FIGS. 6a–6d, represent the contribution of facilitated diffusion of $HbO_2$ to the total oxygen flux, and reveal the character of facilitated diffusion as related to the OECs. The greatest contributions in facilitated transport arise at the steepest portions of the oxygen equilibrium curves, where $HbO_2$ diffuses down its steep gradient as $O_2$ is off-loaded.

Figure 6A:
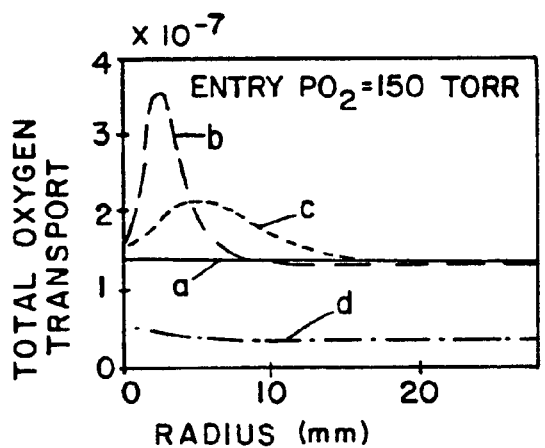
FIG. 6a is a is a plot of the calculated profile of total $O_2$ transport at an entry $PO_2$ of 150 Torr as a function of capillary radius, for a point (dx) down the artificial capillary.
Figure 6B:
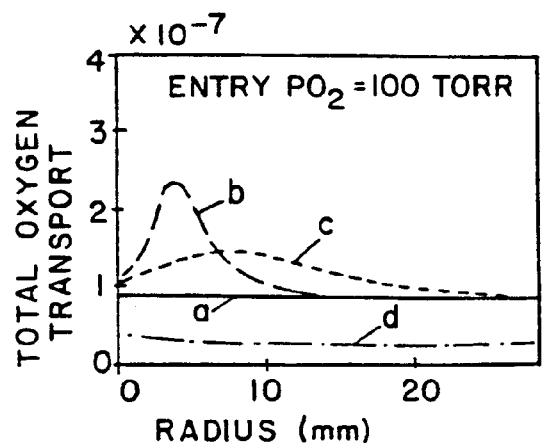
FIG. 6b is a plot of the calculated profile of total $O_2$ transport at an entry $PO_2$ of 100 Torr as a function of capillary radius, for a point (dx) down the artificial capillary.
Figure 6C:
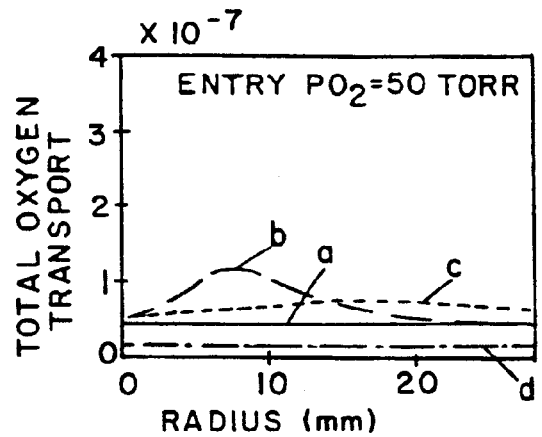
FIG. 6c is a plot of the calculated profile of total $O_2$ transport at an entry $PO_2$ of 50 Torr as a function of capillary radius, for a point (dx) down the artificial capillary.
Figure 6D:
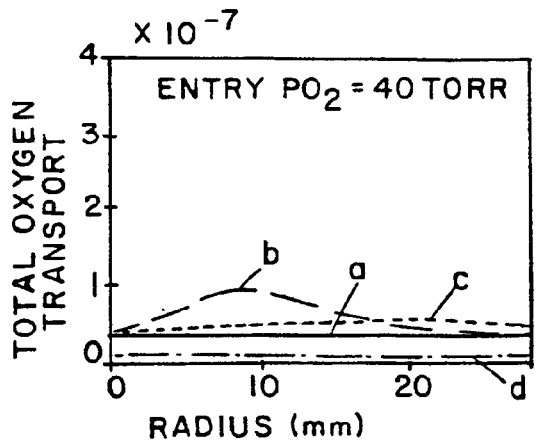
FIG. 6d shows the calculated profile of total $O_2$ transport at an entry $PO_2$ of 40 Torr as a function of capillary radius, for a point (dx) down the artificial capillary.

The individual plots provided in FIGS. 6a, b, c, and d represent cross-sectional fluxes at specific $PO_2$ values, referred to as the entry $PO_2$. Entry $PO_2$ values simulate physiological situations in which blood vessels, of a given diameter, are presented with a RBC or hemoglobin solution at a given $PO_2$. Except for the actual experimental entry point into the artificial capillary where all the samples are air-equilibrated at 150 Torr, the actual transit points, dx, at which the cross-sections are taken for the specific $PO_2$s are not the same, because the rates of $O_2$ exit are different due to different oxygen binding curves and diffusions for the individual samples. The curves were calculated at the dx transit points for each sample in the capillary where the $PO_2$ of interest presented itself.

Figure 7:
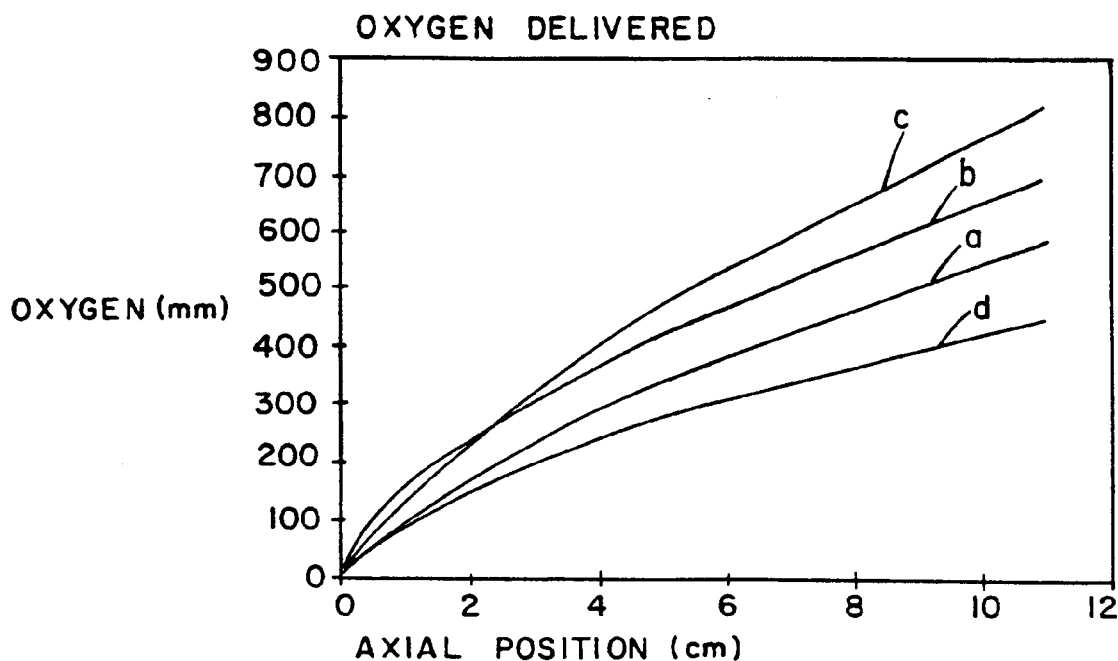
FIG. 7 is a plot of the cumulative oxygen transferred as a function of the axial position in the artificial capillary system.

The data array from the finite element analysis (FEA) is used to plot the progress curves for the liberation of $O_2$ along the axial position of the hollow fiber capillary at a given flow rate, as shown in FIG. 7. This analysis provides a ranking for the amount of $O_2$ that is delivered from the individual samples: $\alpha\alpha$-Hb (curve c)>$HbA_O$ (curve b)>RBCs (curve a)>PEG-Hb (curve d). As explained above, the total $O_2$ delivered is a function of the effective diffusivity reflected by $K^*$ and the shape and position of the individual saturation curves.

Figure 8:
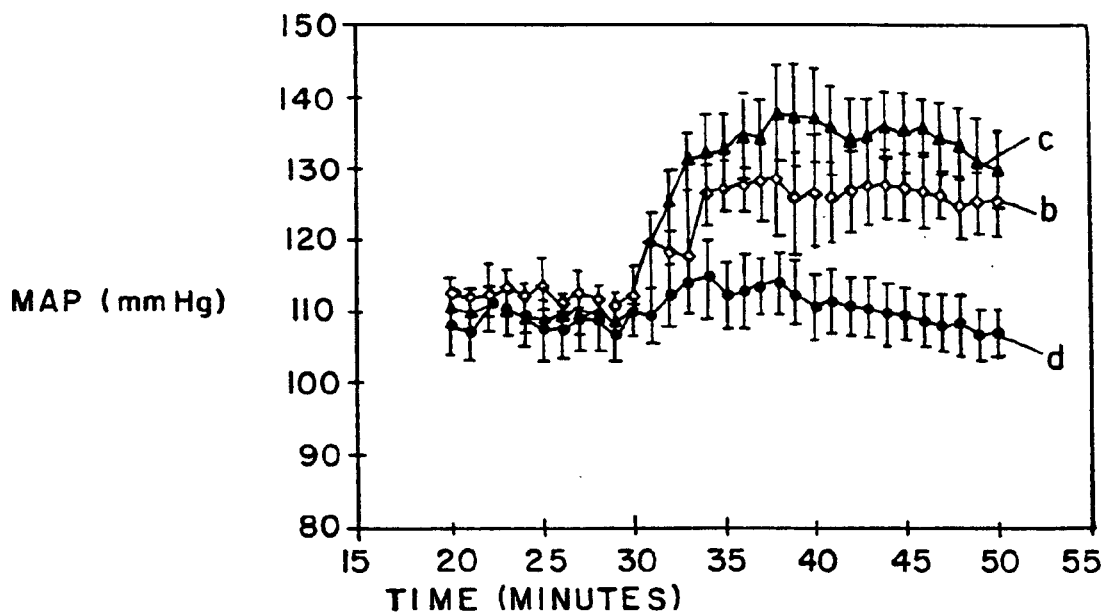
FIG. 8 illustrates mean arterial pressures (MAP) measured in rats after exchange transfusion with the modified hemoglobins being studied.

It has been predicted that if autoregulation occurs as a result of oversupply of oxygen due to facilitated diffusion by cell-free oxygen carriers, the calculated amount of $O_2$ delivered, shown in FIG. 7, should be the greatest for those solutions that show the greatest viscosity. In vivo experiments of 50% exchange transfusion in a rat are consistent with this theory in that the increase in mean arterial pressure during exchange transfusion with cell-free hemoglobins at concentrations similar to those presented in the analyses of FIG. 7. corresponds to the calculated time courses for $O_2$ delivery in the order $\alpha\alpha$-Hb (curve c)>$HbA_O$ (curve b)>PEG-Hb (curve c), shown in FIG. 8.

The method and apparatus of the present invention has been used, with a number of simplifying conditions, to specifically analyze $O_2$ transport out of a well defined artificial blood vessel. The size of the vessel (57 $\mu$m in diameter) is larger than that of the capillaries and more accurately reflects the size of the pre-capillary $A_2$–$A_3$ arterioles. While the artificial blood vessel is devoid of biologic regulatory mechanisms that control arteriolar size through autoregulatory dilation or constriction, this model allows for the study of $O_2$ transport based solely on the physical properties of the oxygen carrying solutions and the geometry of the vessel.

The $O_2$ transport parameter fitted by the mathematical model, $K^*$, is a lumped diffusion constant that accounts for total $O_2$ diffusivity based on the diffusion of molecular oxygen as well as facilitated diffusion due to the gradient of oxyhemoglobin in the vessel. For cell-free solutions, facilitated diffusion plays a significant role because the hemoglobin molecules are not sequestered inside red cell packets. Elimination of the restriction to red cell packets eliminates the intraluminal diffusive resistance to $O_2$ transport and enhances $O_2$ delivery as observed for the cell-free $HbA_O$ and $\alpha\alpha$-Hb solutions. The enhancement is not observed, however, for the PEC-Hb solution, which most likely results from the physical properties of the cell-free solution, including the larger molecular size of the surface-conjugated hemoglobin and the increased viscosity of the solution, which attenuate $O_2$ and Hb $O_2$ diffusivity.

As shown in Equation 6, effective diffusivity, $K^*$, is calculated in terms of $\alpha[PO_2]$, such that the diffusion of oxyhemoglobin is a function of the slope of the OEC: $(\Delta[HbO_2]/\Delta[O_2])\times(\Delta[O_2]/\Delta x)$. Once $HbA_O$ begins to desaturate, it exhibits steep radial gradients for $HbO_2$, which contribute to $HbA_O$'s high fitted values for $K^*$. The overall result for total $O_2$ transferred shown in FIG. 7 at this flow rate reveal that even though $HbA_O$ initially resists desaturation compared with $\alpha\alpha$-Hb, both deliver the same total oxygen after having traveled about halfway down the capillary. In marked contrast, PEG-Hb resists desaturation due, in part, to the shape and position of its oxygen equilibrium curve. Much less $O_2$ is transferred out of the capillary compared to $HbA_O$ and $\alpha\alpha$-Hb, even when it starts to desaturate, which is likely due to the intraluminal resistance to diffusion of both $O_2$ and $HbO_2$ because of increased viscosity and to diffusion of $HbO_2$ because of increased molecular size. The situation then arises that even though $HbA_O$ and PEG-Hb have similar P50's, each exhibits very different total $O_2$ delivery, and even though $HbA_O$ and $\alpha\alpha$-Hb have very different P50's, they exhibit similar quantitative total $O_2$ delivery under these conditions.

The resistance to effective $O_2$ diffusivity by the PEG-Hb solution counteracts the facilitated diffusion of a cell-free hemoglobin solution, which allows the overall $O_2$ delivered by the cell-free PEG-Hb to more closely match that of the total $O_2$ delivered by RBCs in contrast to the increased $O_2$ flux by the non-pegylated hemoglobin. The $O_2$ delivered as measured in the artificial capillary of the present invention corresponds with the physiologic response to such hemoglobins when they are exchange transfused into a rat. The cell-free hemoglobins that deliver more oxygen than RBCs produce increases in mean arterial pressure, which relate to constrictive vasoactivity. PEG-Hb, which quantitatively delivers less $O_2$ in the artificial capillary does not produce a vasoconstrictive response in rats, as indicated by the plots in FIG. 8.

Because all three of the modified hemoglobins have been shown to react with nitric oxide to form nitrosylhemoglobin at the same rate, it is believed that the different vasoresponses to these hemoglobins may reflect autoregulatory blood-flow control. As arterioles sense an overabundance of oxygen delivered by cell-free hemoglobin solutions, they respond by producing autoregulatory constriction. The cell-free PEC-Hb, on the other hand, would not elicit a vasoconstrictive response due to its higher resistance to $O_2$ transport in regulatory blood vessels.

EXAMPLE 2

Carbon Dioxide in Hemoglobin Solution

As in the previous test of oxygen transport, Bis-tris buffer and red blood cells are used as controls for general transport. The test solution should contain no $CO_2$ as it enters the artificial capillary. The exchange gas within the exchange chamber is 92% $N_2$ and 8% $CO_2$, which represents a partial pressure of 56 mmHg. The direction of gas transport in this test is into the capillary. As shown in Table 3, the Bis-tris buffer establishes a baseline to the extent of simple physical absorption with an uncatalyzed hydration reacion. For the Bis-tris system, the resistance to transport is split approximately evenly between the liquid phase and the silicone membrane. A simple aqueous solution (Bis-tris) appears incapable of transporting large amounts of $CO_2$.

TABLE 3

|  | Residence Time (s) | $CO_2$ Pressure (± 2 mmHg) |
|---|---|---|
| Bis-Tris Buffer | 0 | 0 |
| (0.1 M) | 0.367 | 3 |
|  | 0.734 | 4 |
|  | 1.47 | 5 |
| Purified A$_o$-Hemoglobin | 0 | 0 |
| (3.05 mM) | 0.405 | 3 |
|  | 0.81 | 5 |
|  | 1.62 | 6 |
| PEG-Hemoglobin | 0 | 0 |
| (2.5 mM) | 0.394 | 11 |
|  | 0.80 | 22 |
|  | 1.58 | 40 |
| DBBF-Hemoglobin | 0 | 0 |
| (3.03 mM) | 0.398 | 4 |
|  | 0.789 | 5 |
|  | 1.59 | 6 |
| Red Blood Cell | 0 | 0 |
| (3.0 mM) | 0.39 | 11 |
|  | 0.78 | 26 |
|  | 1.56 | 44 |
| Stroma Free-Hemoglobin | 0 | 0 |
| (3.0 mM) | 0.39 | 12 |
|  | 0.78 | 26 |
|  | 1.56 | 46 |

The purified hemoglobin solution (Ao) shows no measurable increase in $CO_2$ pressure. The same is true for a purified hemoglobin that has been chemically cross-linked as with DBBF hemoglobin. The difference between Bis-tris and Ao is only 1 mmHg, within the error of the technique, possibly due to $CO_2$ binding to hemoglobin itself, which is known to occur in vivo.

The $CO_2$-hemoglobin reaction is accomplished within about 100 milliseconds or less. This is within the resident time of the ACTA system. However, there is an important difference between the manner in which this kinetic measurement is made and the ACTA system. $CO_2$-hemoglobin reactions are evaluated with the $CO_2$ already in the solution at an established pressure. For the ACTA system, the gas must first be absorbed before any reaction can occur. In addition, at least in vivo, the hemoglobin-$CO_2$ reaction is favored by the locality of conditions. The red blood cell packages the hemoglobin and $CO_2$ concentrations into a arrangements which favors $CO_2$ binding to hemoglobin (in contrast to $CO_2$ binding to plasma proteins which is insignificant). As with the Bis-tris buffer, the capacity of a simple hemoglobin solution to transport carbon dioxide is limited.

As testing proceeded, it became apparent that the critical factor in allowing a high volume of carbon dioxide transport was presence or lack of carbonic anhydrase. To greatly increase the amount of carbon dioxide transported, the most effective method is to provide a catalyst. Carbonic anhydrase (CAS) provides a tremendous increase in the hydration-dehydration velocity of the $CO_2$-bicarbonate system. This increase in velocity allows the system to obtain equilibrium much more readily than in the absence of CAS. By obtaining equilibrium, the amount of $CO_2$ transported as gas or in the form of bicarbonate greatly increases. For PEG-Hb, at the longest resident time, the $CO_2$ pressure is 40 mmHg and the bicarbonate concentration is 12 mM. This compares with only 6 mmHg $CO_2$ and 2.38 mM bicarbonate for the Ao-Hb solution.

Numerous controls were tested to narrow the possible mechanisms of action seen in the PEG-Hb. First red blood cells were tested. Since they are known to contain CAS, and there was significant transport of $CO_2$, this was a positive indicator. Cell free or stroma free hemoglobin was elevated. Stroma free hemoglobin is merely the contents of the red blood cell with the red blood cell membrane removed. Thus, this solution will contain CAS. This solution displayed $CO_2$ properties nearly identical to RBC.

Figure 10:
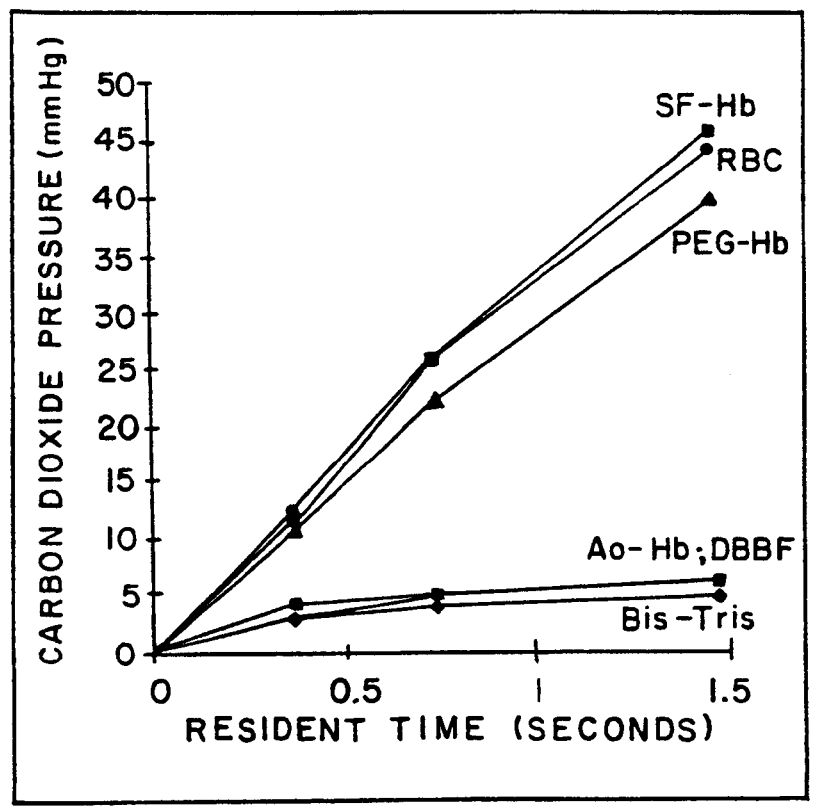
FIG. 10 is a plot of $PCO_2$ with residence time for controls and test solutions.

A comparison of the various solutions is shown in FIG. 10. At the longest resident time, the differences are striking.

Next with respect to the ACTA, the addition of CAS to the control buffer Bis-tris should result in increased transport. As can be seen in Table 4, the addition of CAS to the buffer vastly increased the point to equilibrium. The choice of 13,000 activity units/ml was selected as this is a medium value to the range (between 5,000–20,000 activity units) of concentrations of CAS which is believed to reside in the red blood cell.

To confirm that the CAS was the active agent, acetazolamide (AZ) at a concentration of approximately $10^{-3}$ molar. AZ was added to the stroma free hemoglobin, since this solution was known to contain CAS. The inhibition effect was nearly complete for the level of $CO_2$ pressure dropped to baseline levels found in the Bis-tris control, as seen in Table 4. The experiment was repeated with the PEG-Hb solution and near identical results were obtained.

TABLE 4

|  | Residence Time (s) | $CO_2$ Pressure (± 2 mmHg) |
|---|---|---|
| Bis-Tris with | 0 | 0 |
| Carbonic Anhydrase | 0.3 | 10 |
| (13,000 act unit/ml) | 0.76 | 21 |
|  | 1.52 | 39 |
| Stroma Free-Hemoglobin | 0 | 0 |
| (3.04 mM) with 0.9 mM | 0.39 | 3 |
| Acetazolamide | 0.76 | 5 |
|  | 1.56 | 7 |
| PEG-Hemoglobin | 0 | 0 |
| (2.5 mM) with 1.1 mM | 0.394 | 3 |
| Acetazolamide | 0.788 | 4 |
|  | 1.58 | 6 |

Thus, by using the ACTA, not only is gas transport characterized, but the chemical properties of the solution can be identified.

The important issue with regard to blood substitutes is that carbon dioxide transport can not be ignored. The development of this field has been driven by a focus on oxygen transport as this is seen as the logical first step in the production of artificial blood. Carbon dioxide removal is critical to body homeostasis. Not only does this waste gas need to be removed but $CO_2$, through the bicarbonate system, is the fundamental mechanisms in maintaining body pH. There are other buffering systems but the bicarbonate system is by far the most important. The body must maintain a stable pH at 7.4 with changes no more than±0.6 pH, or death may occur.

The body maintains its pH through two organ systems, the kidney and the lung. The kidney's control of the pH is the slower acting (hours to days) of the two systems and is termed metabolic control. This metabolic system adjusts the pH by secreting hydrogen ions in the urine (removing acid and rising the pH) or by reabsorbing $HCO_3$-ions (adjusting the base). The lung's control is the system for adjustments to rapid changes (within 1 to 10 minutes) in the blood pH. Here, if the blood pH rises above 7.4, the body will respond by slowing breathing. This will reduce removal of $CO_2$ from the blood. The term base excess (BE) is a derived parameter (from the pH, $HCO_3$,- and Hb levels) that characterizes the acid-base balance in the blood. This expression approximates the amount of acid or base (in mmol/l) necessary to titrate 1 liter of blood to pH 7.4 at a $_pCO_2$ of 40 mmHg. A positive BE indicates that the blood is too basic and acid is needed to bring back equilibrium. A negative BE indicates blood that is too acidic and needs a base to return to pH 7.4. The normal range for BE is±5 as necessitating some clinical intervention.

To evaluate the efficacy of these HBBS, an in vivo (with rats) exchange-shock protocol model was developed. In this model, a 50% exchange of blood for the HBBS is accomplished over a 20-minute period through the femoral artery/vein. Immediately following the exchange, the animal is bled of 60% of its blood volume over a period of one hour. The experiment is continued for another hour (total experiment time—2.5 hours) with the animals in a state of shock. The bleed is done to stress the system. The stress assists the evaluation of efficacy of each blood substitutes. One of the most difficult problems with developing a blood substitute is the tremendous capacity of blood to transport oxygen and $CO_2$. It is estimated that a healthy person could lose 75% of his/her RBCs and still survive. Given this over capacity, demonstrating the beneficial effect of a blood substitute is different and requires in vivo protocols which tax the capacity of the blood/substitute solution.

The rat exchange-shock protocol was used to evaluate a number of physiological variables. Two of the parameters measured were the pressure of carbon dioxide ($_pCO_2$) and base excess. In FIG. 11 is the results of the $_pCO_2$ levels with timeline of the experiment. To review, the exchange occurs over the 31 20 minute to 0 point at which time the bleed is started and continued over the first 60 minutes. The control is an animal in which only the shock bleed is done.

There is no exchange or replacement of any fluid lost in the bleed. Pentastarch is a high molecular weight carbohydrate (average molecular weight=120,000 daltons; a glucose polymer) in aqueous solution that possesses a viscosity similar to blood (e.g. 4.0 $_cP$). Its gas carrying capacity is limited to simple dissolving effects of gas in aqueous liquid (Henry's law). Pentastarch is used as a volume replacement for blood and is commercially available through DuPont-Merck as Pentaspan.®

This system is very complex. The most likely answer to graphical information is probably a combination of events. One conceivable explanation for the maintenance of $_pCO_2$ levels by PEG-Hb is as follows. Both alpha—alpha hemoglobin (DBBF) and Pentastarch transport $CO_2$ by an uncatalyzed hydration/solubility effect. However, this as shown by the ACTA is a small level of transport. As residual $CO_2$ is removed by the lungs, the amount entering the solution would be minor since without carbonic anhydrase, the $CO_2$-bicarbonate system to equilibrate, increasing the amount of $CO_2$ transported and maintaining levels of $_pCO_2$. If $CO_2$ is not being transported, one should see a large negative base excess.

A more negative base excess indicates that an excess of $H^+$ ions. If $CO_2$ is not transported, then as the $_pCO_2$ builds up in the tissue, more bicarbonate and $H^+$ ions will be produced. This will result in a large negative base excess. Acid-base balance is critically important for one of the best indicators for survival of shock is the acid-base balance. Notice with the DBBF animals (alpha—alpha) the time points end at 60 minutes. The survivability in this group (of at least 5 rats) was so poor that one can not compare the data after the 60-minute time point (nearly all the animals were dead). With respect to survivability, at 120 minutes, only 10% of the Pentastarch animals were alive. For the controls at 120 minutes, approximately 50% were living. Only the PEG-Hb animals showed excellent survival rates with 90%+ survival at 120 minutes. The situation for pH balance is similar, with PEG-Hb maintaining proper pH better than the controls, which maintained pH better than Pentastarch, which maintain pH better than alpha—alpha.

To summarize with regard to $CO_2$ transport, the conclusions would be; 1) Simple aqueous or hemoglobin solutions will be poor transporters of carbon dioxide in a gas absorption model. This poor transport may lead to improper acid-base balance in the body. 2) to increase carbon dioxide transport, carbonic anhydrase should be contained in the solution. The amount of carbon dioxide transport either as pressure of $CO_2$ or bicarbonate can be increased by a factor of six times when appropriate levels of carbonic anhydrase are added. 3) Survival rates and proper pH maintenance appear greatly improved if the exchange solution has a large capacity to transport carbon dioxide.

The presence of carbonic anhydrase effectively reduces the liquid phase resistance to zero and significantly accelerates the solution towards an equilibrium value. To analyze the effect of carbonic anhydrase (CAS), two chemical modifiers were used: bovine carbonic anhydrase (bCAS), and acetazolamide. The bCAS was used as a positive control to demonstrate how, upon its addition to Bis-tris, there would be an increase in the transport of $CO_2$. Acetazolamide is a specific inhibitor of carbonic anhydrase which should reduce $CO_2$ transport back toward a value close to pure physical absorption (plus a small chemical reaction.) As with oxygen transport, each data point represents a minimum of three measurements. The error associated with the measurement is ±2~3 mmHg, most of which is inherent machine error (1.5 mmHg), with the remainder due to the range of data at each point (approx. 0.5~1 mmHg.)

Concomitant with carbon dioxide transport is a change in the pH of the solution. The Bis-tris buffer is effective in mitigating drastic changes in pH, however, as $CO_2$ is transported into solution, the carbon dioxide-bicarbonate system is far from equilibrium. With reference to Equation 7

$$CO_2 + H_2O \leftrightarrow H_2CO_3 \leftrightarrow H^+ + HCO_3, \qquad (7)$$

$CO_2$ is hydrated immediately to form bicarbonate and hydrogen ions when little or no bicarbonate is in solution. The more $CO_2$ transported, the greater the system tends toward equilibrium, and the greater the overall amount of hydrogen ions produced, causing the solution pH to drop.

The solutions containing carbonic anhydrase exhibited the largest pH changes (e.g., Bis-tris-CAS, PEG-Hb, SF-Hb). Of the hemoglobin solutions, stroma-free hemoglobin transported the highest amount of $CO_2$ and, thus, had the largest pH drop.

While the preceding description of the preferred embodiment and the example provided relate to blood substitutes, it will be apparent to those of skill in the art that the system and method of the present invention have applications which are not limited to analysis of oxygen transport properties in blood, blood substitutes, and mixtures thereof. Gas transport and exchange properties may also be measured in, for example, other biological fluids and matrices, liquid polymers, or fuels, and the gases to be measured can include not only oxygen, but also carbon dioxide, carbon monoxide, nitric oxide, nitrous oxide, helium, and gases used in anesthesia, to name a few. Clinical applications include, but are not limited to, monitoring for anesthesia, septic shock, inhalation of toxic gases.

Using the ACTA, it is possible to determine the gas dissociation properties of a fluid. For example, the oxygen dissociation curve of hemoglobin can be determined assuming the diffusion properties of the hemoglobin are known. Initially, the hemoglobin sample would be treated with oxygen to have a high partial oxygen pressure ($PO_2$). Successive samples are tested, each with a progressively stepped-down or steadily-ramped starting $PO_2$ level, until equilibrium is achieved. The $PO_2$ measured for each sample at the exit is a function of the oxygen dissociation, and the combined results of the different tests can be used to generate an $HbO_2$ dissociation curve, which can be used to indicate, for example, hemoglobin abnormalities.

It will be apparent to those skilled in the art that various modifications and variations may be made in the system and process of the present invention without departing from the spirit or scope of the invention. Thus, it is intended that the present invention cover the modification and variations of this invention provided they come within the scope of the appended claims and their equivalents.

We claim:

1. A system for measuring gas transport in a fluid sample, the system comprising:
    a temperature-controlled environment;
    a dispenser disposed within the temperature-controlled environment for dispensing the fluid sample at a pre-determined flow rate;
    a gas-tight exchange chamber disposed within the temperature-controlled environment;
    a permeable artificial capillary disposed within the exchange chamber and having a first end in fluid connection with the dispenser for receiving the fluid sample, the artificial capillary being adapted to permit gas exchange between the fluid sample within the artificial capillary and an interior of the exchange chamber;
    an exchange gas supply adapted for providing a constant flow of an exchange gas to the exchange chamber;
    a sample collector in fluid communication with a second end of the artificial capillary for receiving an effluent fluid sample; and
    a gas analyzer for determining an amount of gas remaining in the effluent fluid sample.

2. The system of claim 1, wherein said temperature-controlled environment comprises a non-permeable enclosure.

3. The system of claim 1, wherein said dispenser comprises a gas-tight syringe and an infusion syringe pump.

4. The system of claim 1, further comprising:
    at least one temperature probe disposed within the gas exchange chamber for generating a signal representative of a chamber temperature;
    a controller for receiving the signal from the temperature probe; and
    a heating/cooling device for increasing or decreasing an environmental temperature in response to a control signal from the controller, wherein the chamber temperature maintained at a predetermined temperature.

5. The system of claim 4, wherein the fluid sample is blood or a blood substitute.

6. The system of claim 5, wherein the predetermined temperature is 37° C.

7. The system of claim 4, wherein the exchange gas is humidified by bubbling gas from the exchange gas source through a water bath at the predetermined said temperature.

8. The system of claim 4, wherein the gas analyzer is a blood gas analyzer.

9. The system of claim 1, further comprising a flow cell disposed between the dispenser and the gas exchange chamber.

10. The system of claim 9, further comprising at least one gas probe adapted for measuring gas in the fluid sample within the flow cell.

11. The system of claim 10, wherein the gas probe is an oxygen electrode.

12. The system of claim 1, wherein the sample collector comprises:
    a collection cell; and
    a gas-tight syringe in fluid communication with the collection cell.

13. The system of claim 12, further comprising a gas probe adapted for measuring gas in the effluent fluid sample within the collection cell.

14. The system of claim 13, wherein the gas probe is an oxygen electrode.

15. The system of claim 12, further comprising a flow meter inserted within the collection cell for measuring a flow rate of the effluent fluid sample.

16. The apparatus of claim 11 wherein said oxygen flow cell contains a plurality of oxygen probes therein.

17. A method for measurement of transport properties of a gaseous component of a fluid sample, the method comprising:
    obtaining a fluid sample wherein the gaseous component is protected from degradation or reaction and wherein an entrance partial pressure of the gaseous component is calculated or pre-measured;
    conditioning the fluid sample to a predetermined temperature;
    pumping the fluid sample at a pre-selected flow rate through a permeable artificial capillary having a known radius, wherein the artificial capillary is disposed within a gas exchange chamber containing a constant flow of an exchange gas;
    collecting the fluid sample after it has exited the artificial capillary;
    analyzing the fluid sample to determine an exit partial pressure of the gaseous component contained therein; and
    calculating a difference between the entrance and exit partial pressures.

18. The method of claim 17, further comprising maintaining the gas exchange chamber at the predetermined temperature.

19. The method of claim 17, wherein the fluid sample is blood or a blood substitute and the step of analyzing the fluid sample comprises measuring the fluid sample in a blood gas analyzer.

20. The method of claim 19, wherein the gaseous component is oxygen.

21. The method of claim 20, wherein the fluid sample is a cell-free hemoglobin solution.

22. The method of claim 21, further comprising the step of calculating a flux of oxygen according to the relationship $$-J = \frac{D_{O2}\Delta O_2}{\Delta x} + \frac{D_{HbO2}\Delta Y[Hb]_T}{\Delta x}$$

where $D_{O2}$ and $D_{HbO2}$ are diffusion constants for $O_2$ and $HbO_2$, respectively; $\Delta O_2$ is a difference in partial pressure of $O_2$ inside and outside the artificial capillary; $\Delta x$ is an effective wall thickness of the artificial capillary; $\Delta Y$ is a gradient of hemoglobin saturation from an axial center of the artificial capillary to its wall; and $[Hb]_T$ is a total cell-free hemoglobin concentration.

23. The method of claim 19, wherein the artificial capillary has a diameter adapted to approximate in vivo capillary residence times.

24. The method of claim 17, wherein the exchange gas is nitrogen.

25. The method of claim 17, wherein the exchange gas is humidified and conditioned to the predetermined temperature.

26. The method of claim 17, wherein the pre-selected flow rate is adapted to provide a selected residence time within the artificial capillary.

27. The method of claim 17, further comprising the step of calculating a flux of the gaseous component according to Fick's first law.

28. A method for analyzing gas transport properties of a solution containing a plurality of solute molecules and having a viscosity, the method comprising:
   obtaining a sample of the solution having an entrance partial pressure of a target gas is calculated or pre-measured;
   pumping the solution sample at a pre-selected flow rate through a permeable artificial capillary having a length and a radius, wherein the artificial capillary is disposed within a gas exchange chamber containing a constant flow of an exchange gas so that the target gas is diffused out or or into the artificial capillary;
   collecting the solution sample after it has exited the artificial capillary;
   analyzing the fluid sample to determine an exit partial pressure of the target gas contained therein;
   calculating a difference between the entrance and exit partial pressures; and
   calculating a diffusivity according to the relationship $$DS = \frac{kT}{y\eta_a r_b}$$

where k is Boltzman's constant, $\eta_a$ is the viscosity of the solution; $r_b$ is the radius of the solute molecules; $r_a$ is the radius of the solute molecules, and y=6 for $r_b >> r_a$ and y=4 for $r_b \approx r_a$.

29. The method of claim 28, wherein the solution is blood, one or more blood components, or a blood substitute and the solute molecule is $HbO_2$.

30. The method of claim 29, wherein the target gas is oxygen.

31. The method of claim 29, wherein the target gas is carbon dioxide.

32. A method for prediction of in vivo blood pressure response to a hemoglobin-based oxgen carrier (HBOC) solution, the method comprising:
   obtaining a sample of the HBOC solution having an entrance partial oxygen pressure that is calculated or pre-measured;
   pumping the HBOC solution sample at a pre-selected flow rate through a permeable artificial capillary having a length and a radius, wherein the artificial capillary is disposed within a gas exchange chamber containing a constant flow of an exchange gas so that oxygen within the HBOC solution is diffused out of the artificial capillary;
   collecting the solution sample after it has exited the artificial capillary;
   analyzing the fluid sample to determine an exit partial oxygen pressure;
   calculating a difference between the entrance and exit partial oxygen pressures; and
   calculating a diffusivity according to the relationship $$D_{HbO2} = \frac{kT}{y\eta_a r_b}$$

where k is Boltzman's constant, $\eta_a$ is the viscosity of the solution; $r_b$ is the radius of the solute molecules; $r_a$ is the radius of the solute molecules, and y=6 when the solute molecules are hemoglobin and y=4 when the solute molecules are molecular oxygen.

33. A method for measurement of saturation of a target gas within a solution containing a plurality of solute molecules, the method comprising:
   obtaining a sample of the solution having an entrance partial pressure of a target gas is calculated or pre-measured;
   measuring an entrance optical absorption of the solution sample at a wavelength corresponding to presence of the target gas:
   pumping the solution sample at a pre-selected flow rate through a permeable artificial capillary having a length and a radius so that the solution sample has a known residence time within the artificial capillary, wherein the artificial capillary is disposed within a gas exchange chamber containing a constant flow of an exchange gas so that the target gas is diffused out or or into the artificial capillary;
   measuring an exit optical absorption;
   collecting the solution sample after it has exited the artificial capillary;
   analyzing the fluid sample to determine an exit partial pressure of the target gas contained therein;
   calculating a difference between the entrance and exit partial pressures;
   calculating a difference between the entrance and exit optical absorptions and determining a concentration of solute molecules in the solution; and
   determining saturation as a function of the difference in partial pressure, the concentration of solute molecules, and the residence time.

* * * * *